United States Patent
Hayashihara (10) Patent No.: US 7,483,158 B2
(45) Date of Patent: Jan. 27, 2009

(54) IMAGE FORMING APPARATUS FOR FORMING IMAGE ON RECORD MEDIUM

(75) Inventor: Hiromichi Hayashihara, Yokohama (JP)

(73) Assignees: Kabushiki Kaisha Toshiba, Tokyo (JP); Toshiba Tec Kabushiki Kaisha, Tokyo (JP)

( * ) Notice: Subject to any disclaimer, the term of this patent is extended or adjusted under 35 U.S.C. 154(b) by 106 days.

(21) Appl. No.: 11/735,731

(22) Filed: Apr. 16, 2007

(65) Prior Publication Data

US 2008/0252896 A1 Oct. 16, 2008

(51) Int. Cl.
*H04N 1/028* (2006.01)
(52) U.S. Cl. .................................. 358/1.12
(58) Field of Classification Search .................. 430/30; 382/112, 100; 345/166, 163, 157, 156
See application file for complete search history.

(56) References Cited

U.S. PATENT DOCUMENTS

| 6,248,487 B1 * | 6/2001 | Cohn et al. ................... 430/30 |
| 2005/0190157 A1 * | 9/2005 | Oliver et al. ................. 345/166 |
| 2007/0242857 A1 * | 10/2007 | Yamamoto ................... 382/112 |

FOREIGN PATENT DOCUMENTS

JP 2004-294426 10/2004

* cited by examiner

*Primary Examiner*—Mark K Zimmerman
*Assistant Examiner*—James A Bonner, Jr.
(74) *Attorney, Agent, or Firm*—Amin, Turocy & Calvin, LLP (57) ABSTRACT

A laser beam is irradiated on a record medium, a speckle generated by surface scattering is measured by an image sensor, speckle information obtained is subjected to FFT transform, and a paper quality of the record medium is discriminated from a peculiar pattern due to roughness of the surface of the record medium.

9 Claims, 5 Drawing Sheets

IMAGE FORMING APPARATUS FOR FORMING IMAGE ON RECORD MEDIUM

BACKGROUND OF THE INVENTION

1. Field of the Invention

The present invention relates to an image forming apparatus that forms an image on a record medium, the image forming apparatus including a function of discriminating a type and the like of the record medium.

2. Description of the Related Art

In forming an image on a record medium, it may be impossible to perform appropriate image formation if a fixing condition or a conveyance condition is kept fixed. Thus, conventionally, in an image forming apparatus, the fixing condition or the conveyance condition is controlled according to a type of the record medium.

In giving information on the record medium to a control unit of the image forming apparatus, it is conceivable that a user sets classification information of the record medium. However, an image forming apparatus having means for classifying a record medium built therein taking operability into account has been proposed (e.g., JP-A-2004-294426).

This image forming apparatus includes a speckle measuring unit, vibrates a record medium on a conveying path, measures a movement or a change of a speckle due to a movement of the record medium to obtain a vector pattern, compares the vector pattern with speckles stored in a storing unit in association with types of record media, detects a type of the record medium, and changes a recording condition and a fixing condition according to the type of the record medium detected.

BRIEF SUMMARY OF THE INVENTION

It is an object of the present invention to provide an image forming apparatus that forms an image on a record medium, the image forming apparatus having a function of discriminating a type and the like of the record medium.

In an aspect of the present invention, an image forming apparatus that forms an image on a record medium includes:

a light source that irradiates light on the record medium and an image sensor that captures a speckle generated on the record medium by the light;

an FFT transform unit that subjects the speckle obtained by this image sensor to fast Fourier transform (FFT);

a storing unit that stores reference speckle patterns, which are values obtained by subjecting speckles of plural kinds of record media to fast Fourier transform; and a control unit that determines a type of the record medium by comparing a value obtained by subjecting the speckle to FFT transform using the FFT transform unit and the reference speckle patterns stored in the storing unit and sets a condition for image formation according to the type of the record medium determined.

DETAILED DESCRIPTION OF THE INVENTION

Throughout this description, the embodiments and examples shown should be considered as exemplars, rather than limitations on the apparatus and methods of the present invention.

An embodiment of an image forming apparatus according to the present invention will be explained in detail using the drawings.

Figure 1:
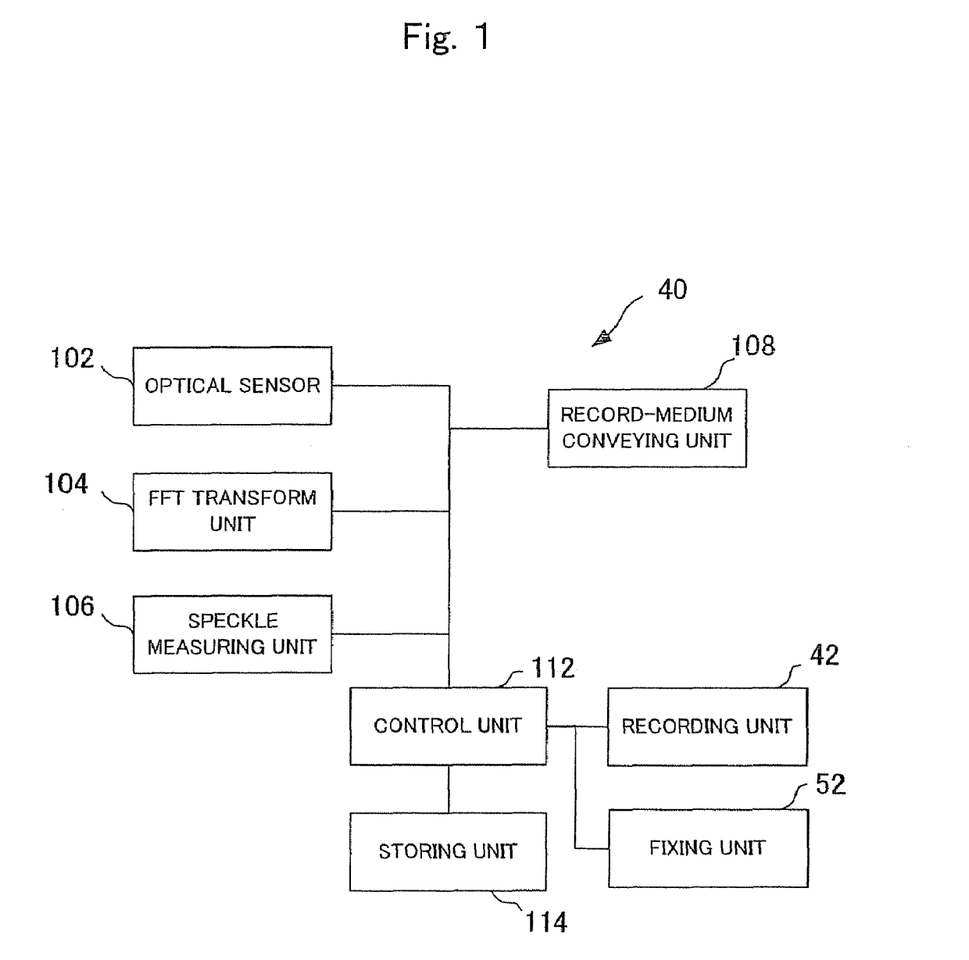
FIG. 1 is a functional block diagram of an image forming apparatus according to an embodiment of the invention.

FIG. 1 is a functional block diagram of an image forming apparatus 501. The image forming apparatus 501 includes an optical sensor 102 that detects a record medium, a speckle measuring unit 106 that measures a speckle of the record medium, an FFT transform unit 104 that subjects the speckle obtained by the speckle measuring unit 106 to fast Fourier transform and analyzes the speckle, a record-medium conveying unit 108 as conveying means for conveying the record medium, a recording unit 42 that records an image on the record medium, and a fixing unit 52 that fixes the image recorded. The image forming apparatus 501 further includes a storing unit 114 that stores information on speckles of record media in association with types of the record media and a control unit 112 that controls the respective units.

Figure 2:
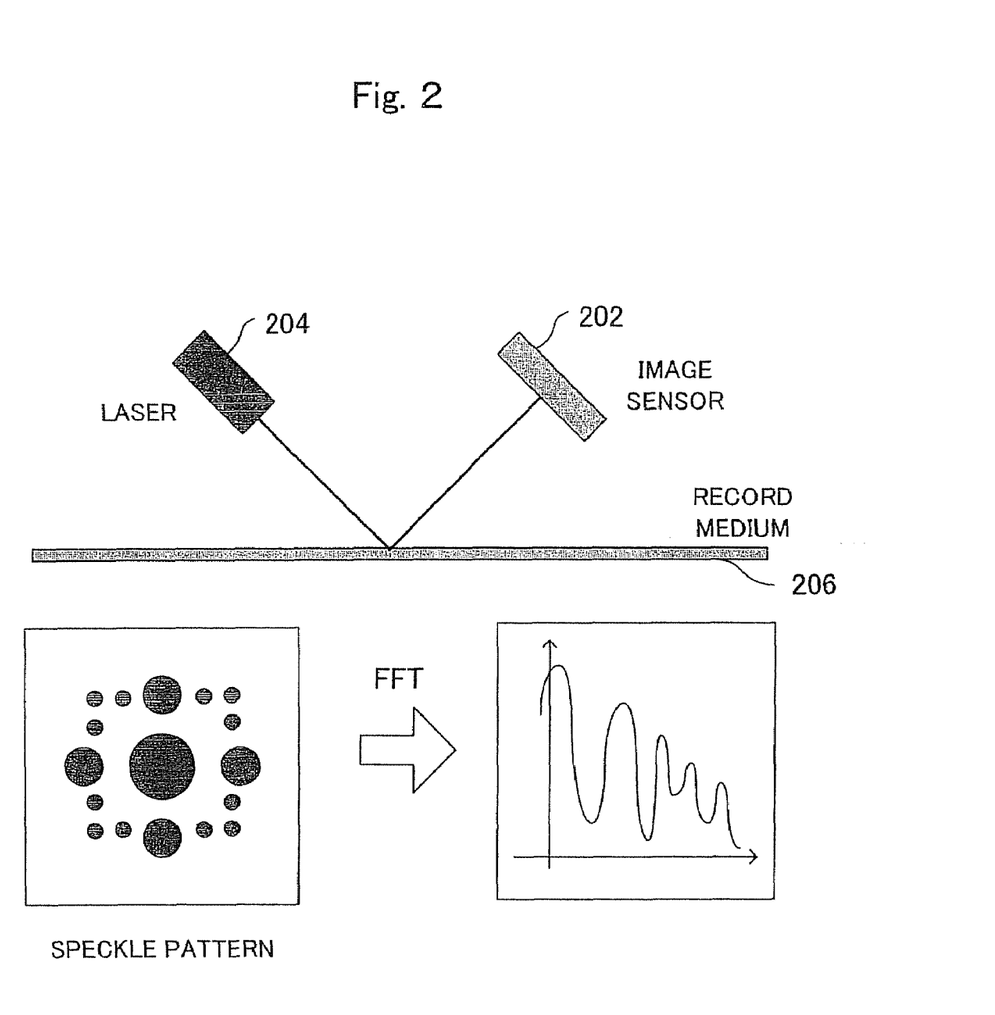
FIG. 2 is a schematic diagram of a structure of a speckle measuring unit according to the embodiment of the invention.

FIG. 2 is a schematic diagram of a structure of the speckle measuring unit 106. As shown in FIG. 2, the speckle measuring unit 106 includes a light source 204 that irradiates predetermined light of a laser or the like on a record medium 206 and an image sensor 202 such as a CCD that images a speckle generated in a place of the record medium 206 irradiated by the light source 204. As the laser, for example, a semiconductor laser is suitable. A lens (not shown) for converting a laser beam irradiated from the semiconductor laser into a desired Gaussian beam may be disposed.

The speckle is a spot-like pattern with high contrast generated by scattering due to a surface of a record medium when the recording medium is irradiated with highly coherent light such as a laser beam. The speckle is peculiar depending on a type of the record medium. Even in record media with the same glossiness, when the record media have different roughness of a record medium surface, i.e., paper qualities are different, peculiar speckles with different distributions (densities) and sizes are generated. Thus, for example, concerning so-called rough paper with paper fiber on a surface thereof relatively roughened, so-called plain paper generally used, and so-called gloss paper with compression of paper fiber sufficiently performed, speckles acquired in advance are subjected to fast Fourier transform and stored in the storing unit 114 in advance in association with the types of the record media. It goes without saying that classification of record media is not limited to this.

In the following explanation, values obtained by subjecting speckles obtained by the speckle measuring unit 106 to fast Fourier transform are referred to as measured speckle patterns and values obtained by subjecting speckles acquired in advance to fast Fourier transform are referred to as reference speckle patterns.

The control unit 112 sequentially reads out the reference speckle patterns from the storing unit 114 and subjects the reference speckle patterns to pattern matching with one measured speckle pattern. Moreover, the control unit 112 determines a type of a record medium corresponding to a reference speckle pattern matching the measured speckle pattern. Compared with a case in which a record medium is vibrated and a speckle is analyzed by cross-correlation on the basis of a change in plural speckle images obtained as in the past, it is possible to perform high-speed processing.

The image sensor 202 such as a CCD and the record medium do not have to be right opposed to each other. This is because the speckle measuring unit 106 does not measure a movement of the record medium. In other words, if an angle of irradiation of a light source on a record medium surface and an angle of reflection to the image sensor 202 such as a CCD are the same, i.e., if light is made incident on the image sensor 202 such as a CCD in specular reflection, a position of the image sensor 202 sensor such as a CCD is not specifically limited.

Figure 3:
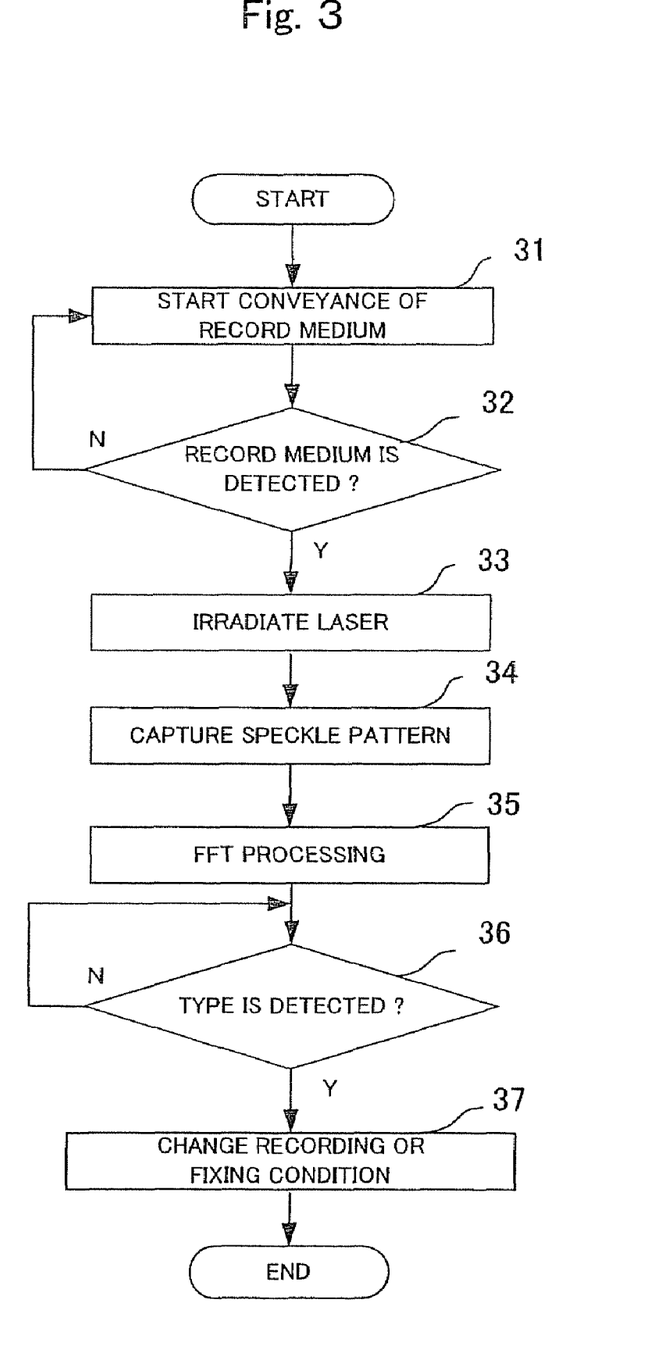
FIG. 3 is a flowchart showing actions of the embodiment of the invention.

Actions of this embodiment will be explained with reference to FIG. 3. FIG. 3 is a flowchart showing the actions of the embodiment of the invention. When a user instructs the image forming apparatus 501 to start recording of an image on the record medium 206 from a control panel (not shown) of the image forming apparatus 501, a personal computer (not shown) connected to the image forming apparatus 501, or the like, type discrimination processing for the record medium 206 is started. In step 31, the record-medium conveying unit 108 of the image forming apparatus 501 starts conveyance of the record medium 206. The record medium 206 is conveyed from a record medium tray 46 along a conveying path.

Subsequently, processing for detecting a record medium 206 is repeated in a predetermined position on the conveying path where the optical sensor 102 is set (step 32).

When the record medium 206 is detected, a laser is irradiated on the record medium 206 (step 33). A speckle generated by surface scattering on the surface of the record medium 206 is scanned by the image sensor 202 such as a CCD (step 34).

Subsequently, the speckle scanned by the image sensor 202 is sent to the FFT transform unit 104. The FFT transform unit 104 subjects this speckle to fast Fourier transform to generate a measured speckle pattern (step 35). FFT processing is executed in order to extract which frequency components and how many frequency components are included in an image signal scanned by the sensor. Since an input waveform is divided into several groups and subjected to arithmetic processing, the processing is fast and it is unlikely that performance of the image forming apparatus implemented with a type discriminating function for record media is deteriorated.

Subsequently, the control unit 112 repeats processing for detecting a type of the record medium 206 until the type of the record medium 206 is detected according to the pattern matching (step 36). Since it is possible to adopt a well-known method as a method itself of the pattern matching, the method is not described in detail here. For example, reference speckle patterns are stored in the storing unit 114 in advance in association with types of the record media and the control unit 112 sequentially reads out the reference speckle patterns stored in the storing unit 114 and compares the reference speckle patterns with the measured speckle pattern generated by subjecting the speckle to the FFT processing in step 35. The control unit 112 determines that a type of a record medium associated with a reference speckle pattern matching the measured speckle pattern is a type of the record medium 206. In this embodiment, since a pattern (a size or a density) of the speckle is observed, it is possible to improve detection accuracy of type discrimination for the record medium 206.

When the type of the record medium 206 is detected, the control unit 112 changes, for example, a recording condition for an image in the recording head 42 and a fixing condition for the recorded image in the fixing unit 52 (step 37) and the processing ends.

A table in which fixing conditions, conveyance conditions, and the like corresponding to types of record media are associated with one another is stored in the storing unit 114 in advance. The control unit 112 reads out a fixing condition, a conveyance condition, and the like from this table on the basis of the type of the record medium 206 detected in step 36 to thereby change the fixing condition, the conveyance condition, and the like according to the type of the record medium 206.

For example, when the control unit 112 determines that the record medium 206 is thick coat paper, the control unit 112 sets a fixing amount small and sets a conveyance speed of the record medium low as a fixing condition.

Light irradiated on the record medium 206 from the light source 204 in order to generate a speckle is not limited to a laser. The light may be any light appropriate for generating a speckle. A speckle is generated according to a characteristic of interference of light, i.e., coherence of light. Even if a light source is not a laser, coherent light is obtained if the light source is a single-color light source. In general, in a light source other than the laser, a coherence length of the light source is small. When an optical distance from the light source to a record medium is shorter than the coherence length, a speckle is generated. Otherwise, a speckle is not generated. Thus, as a condition for the light source, "light should have a coherence length sufficient for generating a speckle". As a light source having the sufficient coherence length other than the laser, there are "luminescence line of krypton" and the like.

As described above, the image forming apparatus 501 can discriminate record media including different record media having the same glossiness on surfaces thereof, a transparent film, which is not a sheet, and the like.

The optical sensor 102 that detects presence of the record medium 206 is arranged in an appropriate place further upstream than the speckle measuring unit 106 on the conveying path of record media in the image forming apparatus. When the speckle measuring unit 106 measures a speckle on the record medium 206, by stopping the record-medium conveying unit 108, the control unit 112 may measure a speckle on the record medium 206 in a state in which the record medium 206 is not conveyed. The control unit 112 may measure a speckle in a state in which the record medium 206 is conveyed without stopping the record-medium conveying unit 108.

As described above, according to the image forming apparatus according to this embodiment, it is possible to accurately discriminate a type of a record medium and perform image formation suitable for the record medium. Since discrimination of a type of a record medium is performed accurately and at high speed, it is unlikely that performance of the image forming apparatus is deteriorated.

A structure of the image forming apparatus and a setting position of the speckle measuring unit 106 in the image forming apparatus will be explained.

Figure 4:
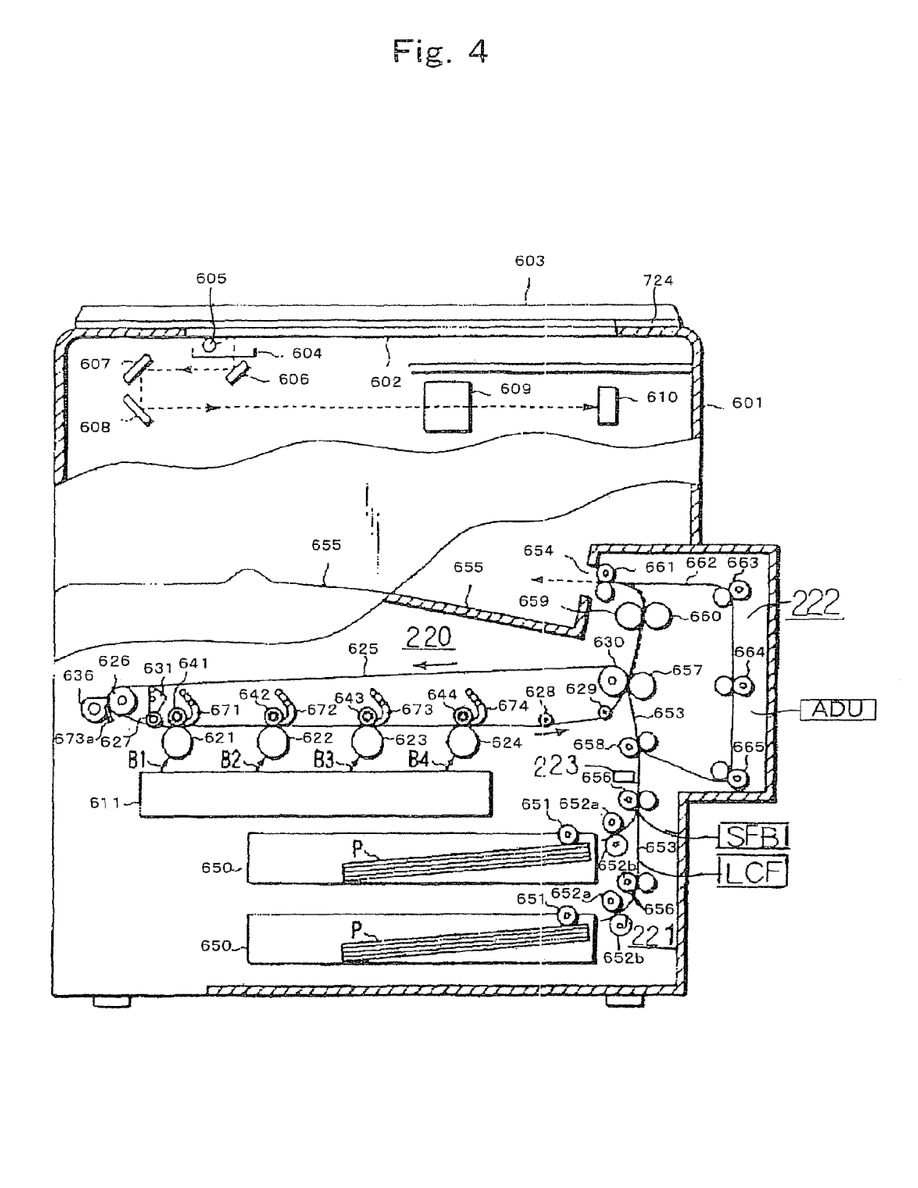
FIG. 4 is a diagram showing an example of a structure of the image forming apparatus according to the embodiment of the invention.

FIG. 4 is a diagram showing an example of a structure of the image forming apparatus 501. As shown in FIG. 4, an original stand 602 for original placement formed of a transparent material such as a glass plate is provided in an upper part of an apparatus main body 601. A cover 603 is set in the apparatus main body 601 to be freely opened and closed to cover this original stand 602.

A scan unit (not shown) that optically scans an image of an original placed on the original stand 602 is provided on a lower surface side of the original stand 602 in the apparatus main body 601. For example, this scan unit has a carriage 604, reflecting mirrors 606, 607, and 608 that reflect light of an exposure lamp 605 reflected on the original, a lens block for magnification 609 that changes a magnification of this reflected light, and a CCD (Charge Coupled Device) 610. The carriage 604 includes the exposure lamp 605 that irradiates light to the original stand 602 and is constituted to be reciprocatingly movable along the lower surface of the original stand 602.

The carriage 604 exposes the original placed on the original stand 602 to light by reciprocatingly moving while lighting the exposure lamp 605. A reflected light image of the original placed on the original stand 602 obtained by this exposure is projected on the CCD 610 through the reflecting mirrors 606, 607, and 608 and the lens block for magnification 609. The CCD 610 outputs an image signal corresponding to the reflected light image of the original projected.

An image forming unit 220 is provided below the scan unit in the apparatus main body 601. The image forming unit 220 includes, for example, a print engine (not shown) and a process unit (not shown).

The print engine includes an exposure unit 611. The process unit includes photoconductive drums 621, 622, 623, and 624 arranged along the exposure unit 611, an endless transfer belt 625 arranged to be opposed to the exposure unit 611 across the photoconductive drums 621, 622, 623, and 624, a drive roller 626 that drives the transfer belt 625, primary transfer rollers 641, 642, 643, and 644 arranged to be opposed to the photoconductive drums 621, 622, 623, and 624 across the transfer belt 625, and a transfer-roller driving unit that drives the primary transfer rollers 641, 642, 643, an 644.

The transfer belt 625 is laid over the drive roller 626, guide rollers 627, 628, and 629, and a driven roller 630 and receives power from the drive roller 626 to rotate and travel in a counterclockwise direction. The guide roller 627 is provided to freely move up and down and receives rotation of a cam 631 to move to the transfer belt 625 side. Consequently, the guide roller 627 displaces the transfer belt 625 to the side of the photoconductive drums 621, 622, 623, and 624.

This image forming unit 220 executes an image forming process for forming an image based on image data (an image signal outputted from the CCD 610) and printing the image on a record medium being conveyed. The image signal outputted from the CCD 610 is supplied to the exposure unit 611 after being appropriately processed. The exposure unit 611 emits a laser beam B1 corresponding to an image signal of a yellow color to the photoconductive drum 621 for the yellow color, emits a laser beam B2 corresponding to an image signal of a magenta color to the photoconductive drum 622 for the magenta color, emits a laser beam B3 corresponding to an image signal of a cyan color to the photoconductive drum 623 for the cyan color, and emits a laser beam B4 corresponding to an image signal of a black color to the photoconductive drum 624 for the black color.

The primary transfer rollers 641, 642, 643, and 644 are moved (lowered) to the transfer belt 625 side to bring the transfer belt 625 into contact with the photoconductive drums 621, 622, 623, and 624 and transfer visible images on the photoconductive drums 621, 622, 623, and 624 onto the transfer belt 625.

A drum cleaner, a charge removing lamp, a charging unit, and a developing unit, which are not shown in the figure, are disposed in order around the photoconductive drum 621. The drum cleaner has a drum cleaning blade set in contact with the surface of the photoconductive drum 621 and scrapes off a developing material remaining on the surface of the photoconductive drum 621 with the drum cleaning blade.

The charge removing lamp removes charges remaining on the surface of the photoconductive drum 621. The charging unit charges the surface of the photoconductive drum 621 with electrostatic charges by applying a high voltage to the photoconductive drum 621. The laser beam B1 emitted from the exposure unit 611 is irradiated on the surface of the photoconductive drum 621 subjected to this charging. According to this irradiation, an electrostatic latent image is formed on the surface of the photoconductive drum 621. The developing unit visualizes the electrostatic latent image on the surface of the photoconductive drum 621 by supplying a developing material (a toner) of the yellow color to the surface of the photoconductive drum 621.

In the other photoconductive drums 622, 623, and 624, electrostatic latent images on the surfaces of the respective photoconductive drums 622, 623, and 624 are visualized using developing materials of colors corresponding thereto, respectively, in the same manner.

A cleaner 636 is provided across the transfer belt 625 in a position of the image forming unit 220 opposed to the drive roller 626. This cleaner 636 has a cleaning blade 636a set in contact with the transfer belt 625 and scrapes off a developing material remaining on the transfer belt 625 with the cleaning blade 636a.

Printing modes are changed as follows. Hooks 671, 672, 673, and 674 are provided near the primary transfer rollers 641, 642, 643, and 644. The hooks 671, 672, 673, and 674 engage with shafts of the primary transfer rollers 641, 642, 643, and 644 to lift the shafts while rotating and moves the primary transfer rollers 641, 642, 643, and 644 in a direction apart from the photoconductive drums 621, 622, 623, and 624. Printing modes such as a full color mode, a full separation mode, and a monochrome mode are changed by not moving all the primary transfer rollers 641, 642, 643, and 644 or changing a combination of the primary transfer rollers to be moved.

A storing mechanism and a supplying mechanism for record media will be explained. Plural record medium cassettes 650 that store record media are provided below the exposure unit 611. In these record medium cassettes 650, a large number of record media P of record medium types different from one another are stored in a stacked state. Record-medium supplying mechanisms 221 that supply the record media in the record media cassettes 650 one by one from the top thereof are provided in exit sections (on the right side in the figure) of these record medium cassettes 650, respectively. The record media P are taken out one by one from any one of the record medium cassettes 650 by this record-medium supplying mechanism 221. This record-medium supplying mechanism 221 for taking out the record media includes a pickup roller 651, a record-medium supplying roller 652a, and a separating roller 652b and separates the record media P taken out from the record medium cassette 650 one by one and supplies the record media P to a record-medium conveying path 653.

A conveying path for record media will be explained. The record-medium conveying path 653 extends to a record-medium discharge port 654 in an upper part through the driven roller 630 of the image forming unit 220. The record-medium discharge port 654 faces a record-medium discharging unit 655 extending to an outer peripheral surface of the apparatus main body 601. Conveying rollers 656 are provided near the record-medium supplying mechanisms 221, respectively, on the starting end side of the conveying path 653. When record media are supplied to this record-medium conveying path 653 by any one of the record-medium supplying mechanisms 221, this record-medium conveying path 653 conveys the supplied record medium to the record-medium discharging unit 655.

A secondary transfer roller 657 is provided in a position opposed to the driven roller 630 across the transfer belt 625 along the record-medium conveying path 653. Registration rollers 658 are provided in a position just before the driven roller 630 and the secondary transfer roller 657 in the conveying direction.

The registration rollers 658 feed the record medium P to a space between the transfer belt 625 and the secondary transfer roller 657 at timing synchronizing with a transfer operation, which is an operation for transferring an image formed by a developing material (a toner) onto a record medium, by the transfer belt 625 and the secondary transfer roller 657. The secondary transfer roller 657 transfers, while nipping the record medium P fed from the registration rollers 658 between the secondary transfer roller 657 and the transfer belt 625 on the driven roller 630, a visible image formed by the developing material (the toner) transferred on the transfer belt 625 to this record medium P and prints the visible image. In this way, the registration rollers 658 convey the record medium P to the image forming unit 220 having the transfer belt 625 and the secondary transfer roller 657 in synchronization with the transfer operation of the image forming unit 220.

A heat roller 659 for heat fixing and a press contact roller 660 set in contact with this heat roller 659 are provided in a position further on a downstream side than the second transfer roller 657 of the record-medium conveying path 653. The image transferred on the record medium P is fixed by the heat roller 659 and the press contact roller 660. A record-medium discharge roller 661 is provided at the end of the record-medium conveying path 653.

An automatic duplex unit (hereinafter referred to as ADU) 222 may be provided in the apparatus main body 601. The ADU 222 is set to couple a sub-conveying path 662, which is a path for conveying the record medium P in the ADU 222, to the end of the record-medium conveying path 653 and an entrance to the registration rollers 658. The sub-conveying path 662 branches from a downstream side with respect to the image forming unit 220 of the record-medium conveying path 653 (the end of the record-medium conveying path 653) and joins an upstream side with respect to the image forming unit 220 of this record-medium conveying path 653 (an upstream side position of the registration rollers 658).

This sub-conveying path 662 reverses the front and the rear of the record medium P for duplex printing. Record-medium supplying rollers 663, 664, and 665 are provided in the sub-conveying path 662. The ADU 222 feeds backward the record medium P conveyed from the image forming unit 220 to the record-medium discharging unit 655, conveys the record medium P through the sub-conveying path 662, and causes the record medium P to join the record-medium conveying path 653 on the upstream side of the image forming unit 220. When the record medium P is conveyed in this way, the front and the rear of the record medium P are reversed.

After joining the record-medium conveying path 653, the record medium P returned to the upstream side of the image forming unit 220 by the sub-conveying path 662 is fed into a transfer position where transfer belt 625 and the second transfer roller 657 are in contact by the registration rollers 658 in synchronization with the transfer operation of the image forming unit 220. In this way, the visible image on the transfer belt 625 is also transferred onto the rear surface of the record medium P and printed.

When duplex printing is designated by an operation panel 724 provided in the apparatus main body 601 or a computer or the like connected to the apparatus main body 601 through a network, the sub-conveying path 662 of the ADU 222 comes into a state in which the ADU 222 performs the operation for reversing the front and the rear of the record medium P.

Devices additionally provided will be explained. In the example of the apparatus main body 601 shown in FIG. 4, the two record medium cassettes 650 are provided as supply sources of record media. Three or more record medium cassettes 650 may be provided in the apparatus main body 601. Besides, although not shown in the figure, it is also possible to provide a manual-feed record-medium supplying mechanism (hereinafter referred to as SFB) and a large-capacity record medium feeder (hereinafter referred to as LCF), which is a record-medium supplying mechanism that can store several thousands record media in a stacked state. The SFB and the LCF are set in the apparatus main body 601 such that paths for supplying record media stored therein join the record-medium conveying path 653.

Figure 5:
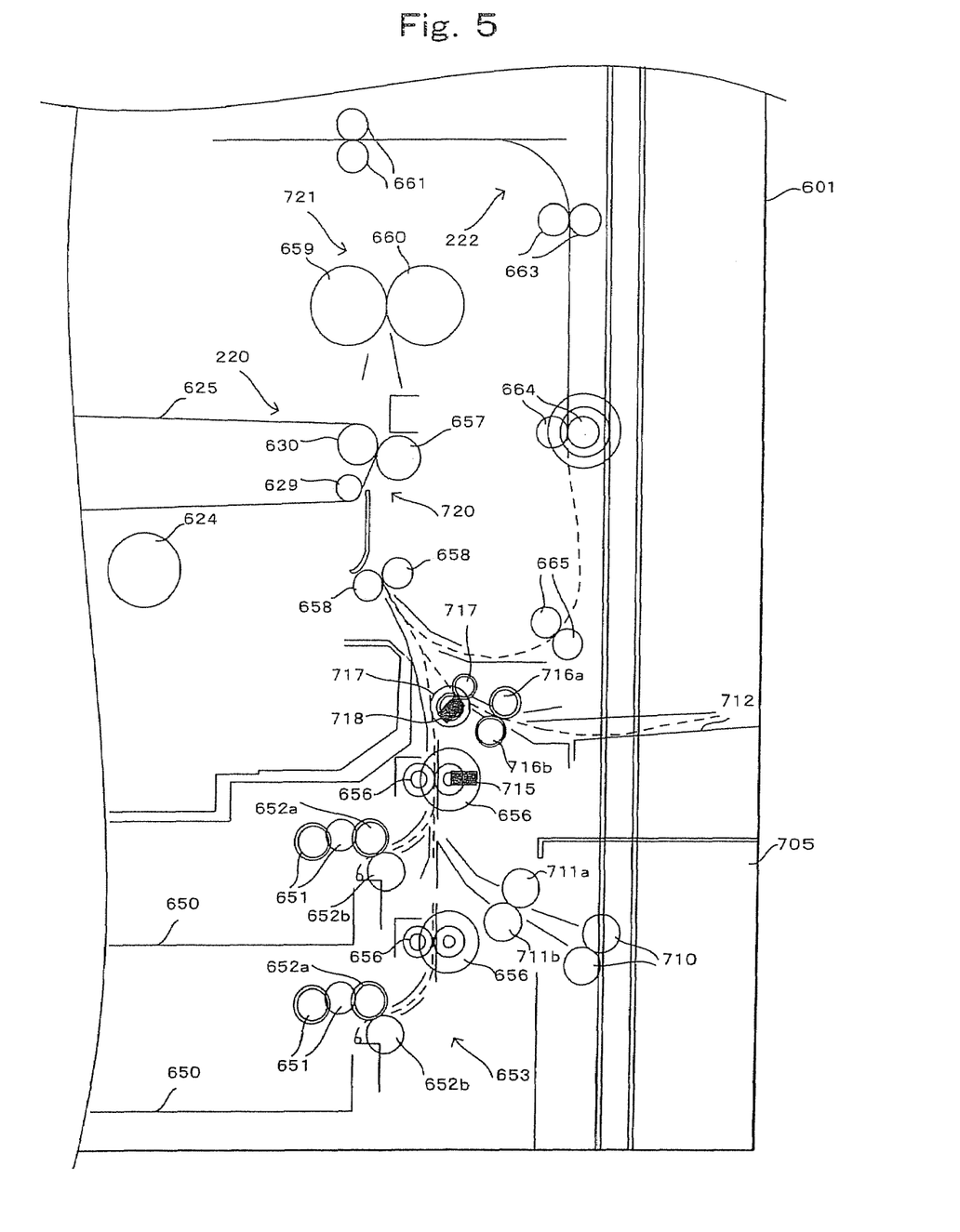
FIG. 5 is a diagram showing a section near a record-medium conveying path in detail.

A setting position of the speckle measuring unit 106 according to this embodiment will be explained. FIG. 5 is a diagram showing a section near the record-medium conveying path 653 in detail. The heat roller 659 and the press contact roller 660 will be hereinafter collectively referred to as a fixing unit 721. When the heat roller 659 heats the record medium P having the developing material (the toner) transferred thereon and the press: contact roller 660 conveys the record medium P while applying a pressure thereto, this fixing unit 721 fixes the developing material on the record medium P.

A not-shown control unit is provided in the apparatus main body 601. It is possible to constitute this control unit using, for example, a CPU, memories such as a ROM and a RAM, and an LSI. The control unit controls the temperature of the heat roller 659. For example, when there is no signal from the control unit, the heat roller 659 stays on standby while maintaining a temperature set in advance according to a type of the record medium P. When a signal for starting fixing is received, the heat roller 659 changes the temperature in accordance with an instruction of the signal.

Since the apparatus main body 601 performs the fixing of the developing material by adopting such a constitution, the speckle measuring unit 106 is set further on the upstream side than the fixing unit 721 of the record-medium conveying path 653.

When only one speckle measuring unit 106 is used, the speckle measuring unit is set in a first setting position 223 shown in FIG. 4. The first setting position 223 is a position on the upstream side with respect to the image forming unit 220 of the record-medium conveying path 653 and further on the upstream side than the registration rollers 658. When an SFB 712 or an LCF 705 is set, the first setting position 223 is a position further on the downstream side than joining points of record-medium supplying paths from the SFB 712 and the LCF 705 and the record-medium conveying path 653. The speckle measuring unit 106 is set to face a surface of a record medium conveyed.

By arranging the speckle measuring unit 106 in this first setting position 223, it is possible to detect types of the record media P conveyed on the record-medium conveying path 653 from all the supply sources of record media using one speckle measuring unit 106.

Depending on a model of the image forming apparatus 501, it may be impossible to set the speckle measuring unit 106 in the first setting position 223 because of a relation of arrangement of the various components in the apparatus main body

601. In some models, the SFB 712 is attached as an option. In these cases, it is also possible to provide the speckle measuring unit 106 in the following two positions.

The positions will be explained using FIG. 5. In the record-medium conveying path 653, a second setting position 715 is a position further on the upstream side than the image forming unit 220 of the record-medium conveying path 653 and further on the upstream side than the registration rollers 658 and a position on the downstream side of the record-medium supplying roller 652*a* and the separating roller 652*b* of the cassette device 650 at an uppermost stage and further on the downstream side than the joining position of the record-medium supplying path from the LCF 705 and the record-medium conveying path 653. The speckle measuring unit 106 is set to face a surface of a record medium conveyed. The speckle measuring unit 106 may be set near the conveying rollers 656 in the second setting position 715.

A third setting position 718 is a position further on the upstream side than the joining position of the record-medium supplying path from the SFB 712 and the record-medium conveying path 653. The speckle measuring unit 106 is set to face a surface of a record medium conveyed. The speckle measuring unit 106 may be set near conveying rollers 717 in the third setting position 718.

By arranging the speckle measuring unit 106 in the second setting position 715 and the third setting position 718, in a model in which the SFB 712 is attached as an option, there is an effect that it is possible to set the speckle measuring unit 106 in the setting position 718 when necessary.

An applied example concerning processing of a signal of a determination result outputted from the speckle measuring unit 106 will be explained. The operation panel 724 used for selecting a type of the record medium P and used for input in the case of display of information and data setting is attached to an upper surface of the apparatus main body 601. The operation panel 724 is connected to the control unit. This control unit controls speed of a motor that drives to rotate the respective rollers for conveying a record medium and also performs stop and restart of conveyance of the record medium.

First, the control unit stores a default type of a record medium or a type of a record medium inputted through the operation panel 724 in a memory serving as a setting record medium and sets a standby temperature of the heat roller 659 corresponding to this setting record medium.

When the record medium P is conveyed and the speckle measuring unit 106 determines a type of the record medium P, the speckle measuring unit 106 outputs a signal of a determination result to the control unit. The control unit sets, for example, a conveying speed of a record medium, a rotation speed of the fixing unit 721, and the temperature at the time of fixing of the heat roller 659 in accordance with the determination result and transmits an instruction to these devices.

As described above, the image forming apparatus 501 in this applied example sets the setting record medium first and, then, further sets conditions such as speed and temperature at the time of fixing in accordance with a type of a record medium determined by the speckle measuring unit 106. Therefore, there is an effect that it is possible to quickly perform more detailed condition setting at the time of the fixing and execution of the fixing corresponding to the type of the record medium.

Although exemplary embodiments of the present invention have been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claims is:

1. An image forming apparatus that forms an image on a record medium, comprising:
    a light source that irradiates light on the record medium and an image sensor that captures a speckle generated on the record medium by the light;
    an FFT transform unit configured to subject the speckle obtained by this image sensor to fast Fourier transform (FFT);
    a storing unit configured to store reference speckle patterns, which are values obtained by subjecting speckles of plural kinds of record media to fast Fourier transform; and
    a control unit configured to determine a type of the record medium by comparing a value obtained by subjecting the speckle to FFT transform using the FFT transform unit and the reference speckle patterns stored in the storing unit and set a condition for image formation according to the type of the record medium determined.

2. An image forming apparatus according to claim 1, wherein the light source is a laser beam.

3. An image forming apparatus according to claim 1, wherein the light source is luminescence line of krypton.

4. An image forming apparatus according to claim 1, wherein the image sensor is a CCD sensor.

5. An image forming apparatus according to claim 1, wherein an angle of irradiation of the light source on a record medium surface and an angle of reflection to the image sensor are the same.

6. An image forming apparatus according to claim 1, wherein a type of the record medium is discriminated according to pattern matching.

7. An image forming apparatus according to claim 1, further comprising a fixing unit configured to fix an image recorded by the recording means on the record medium, wherein
    the image sensor captures the speckle before the image recorded on the record medium is fixed in the fixing unit.

8. An image forming apparatus according to claim 1, wherein the control unit changes a fixing condition on the basis of the type of the record medium determined.

9. An image forming apparatus that forms an image on a record medium, comprising:
    a record-medium supplying mechanism that supplies record media one by one;
    a record-medium conveying path that conveys the record medium supplied by the record-medium supplying mechanism to a record-medium discharging unit;
    an image forming unit configured to be arranged further on an upstream side than the record-medium discharging unit of the record-medium conveying path and execute an image forming process for printing an image based on image data on the record medium conveyed by the record-medium conveying path;
    a fixing unit configured to fix a developing material on the record medium with a predetermined temperature;
    a light source that irradiates light on the record medium and an image sensor that captures a speckle generated on the record medium by the light, the light source and the image sensor being provided further on the upstream side of the record-medium conveying path than the fixing unit;
an FFT transform unit configured to subject the speckle obtained by the image sensor to fast Fourier transform (FFT);
a storing unit configured to store reference speckle patterns, which are values obtained by subjecting speckles of plural kinds of record media to fast Fourier transform; and a control unit configured to determine a type of the record medium by comparing a value obtained by subjecting the speckle to FFT transform using the FFT transform unit and the reference speckle patterns stored in the storing unit and set a condition in executing the image formation process according to the type of the record medium determined.

* * * * *